(12) United States Patent
Sano et al.

(10) Patent No.: US 11,179,124 B2
(45) Date of Patent: Nov. 23, 2021

(54) X-RAY PHASE IMAGING METHOD

(71) Applicant: Shimadzu Corporation, Kyoto (JP)

(72) Inventors: Satoshi Sano, Kyoto (JP); Koichi Tanabe, Kyoto (JP); Yukihisa Wada, Kyoto (JP); Satoshi Tokuda, Kyoto (JP); Akira Horiba, Kyoto (JP); Naoki Morimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 17/008,021

(22) Filed: Aug. 31, 2020

(65) Prior Publication Data
US 2021/0161492 A1     Jun. 3, 2021

(30) Foreign Application Priority Data
Nov. 29, 2019    (JP) .............................. JP2019-216750

(51) Int. Cl.
*G01N 23/041*      (2018.01)
*A61B 6/00*            (2006.01)

(52) U.S. Cl.
CPC ............ *A61B 6/484* (2013.01); *A61B 6/4035* (2013.01); *A61B 6/463* (2013.01); *A61B 6/5205* (2013.01)

(58) Field of Classification Search
CPC .... G01N 23/0441; G01B 11/25; A61B 6/484; A61B 6/4035; A61B 6/463; A61B 6/5205; A61B 6/4291; A61B 6/4452
See application file for complete search history.

(56) References Cited

U.S. PATENT DOCUMENTS

2018/0356355 A1    12/2018    Momose et al.

FOREIGN PATENT DOCUMENTS

JP        2017-044603 A      3/2017
JP        WO2020188856 A1 *    3/2019

* cited by examiner

*Primary Examiner* — Don K Wong
(74) *Attorney, Agent, or Firm* — Muir Patent Law, PLLC

(57) ABSTRACT

An X-ray phase imaging method includes a step of correcting a gradation that occurred along an orthogonal direction to a translation direction as viewed from an optical axis direction of X-rays in a phase-contrast image based on a distribution state of the gradation.

11 Claims, 12 Drawing Sheets

Phase-contrast Image After Correction 16  200

18  Phase-contrast Image After Correction

Phase-contrast image generation processing

X-RAY PHASE IMAGING METHOD

CROSS-REFERENCE TO RELATED APPLICATIONS

The related application number JP2019-216750, entitled "X-ray phase imaging apparatus", filed on Nov. 29, 2019, invented by Satoshi Sano, Koichi Tanabe, Yukihisa Wada, Satoshi Tokuda, Akira Horiba, and Naoki Morimoto, upon which this patent application is based is hereby incorporated by reference.

BACKGROUND OF THE INVENTION

Field of the Invention

The present invention relates to an X-ray phase imaging method.

Description of the Background Art

Conventionally, an X-ray phase imaging apparatus is known in which a subject is imaged while relatively translating the subject and an imaging system. Such an apparatus is disclosed in, for example, Japanese Unexamined Patent Application Publication No. 2017-44603.

In the above-described Japanese Unexamined Patent Application Publication No. 2017-44603, a radiological examination apparatus (X-ray phase imaging apparatus) is disclosed in which a radiation source unit, a grating group, a detection unit, a transfer unit, and an image generation unit are provided to capture an image of a sample (subject). The radiological examination apparatus is configured to image a sample while translating the sample with respect to the radiation source unit, the grating group, and the detection unit (imaging system) by the transfer unit. Further, the radiological examination apparatus is configured to generate a radiation image (phase-contrast image) by the image generation unit based on a plurality of intensity distribution images acquired while translating the sample by the transfer unit with respect to the radiation source unit, the grating group, and the detection unit by the transfer unit.

Here, although not specifically described in the above-described Japanese Unexamined Patent Application Publication No. 2017-44603, the inventors of the present application have newly discovered that in the case of generating a phase-contrast image based on a plurality of images acquired while relatively translating the subject and the imaging system as in the radiological examination apparatus described in the above-described Japanese Unexamined Patent Application Publication No. 2017-44603, there is a problem (issue) that the phase-contrast image becomes difficult to see because a gradation (gradual change in color tone, brightness, etc.) that occurred along a direction orthogonal to the translation direction as viewed from the optical axis direction of the X-rays in the phase-contrast image.

SUMMARY OF THE INVENTION

The present invention has been made to solve the problems newly discovered by the inventors of the present invention as described above, and an object of the present invention is to provide an X-ray phase imaging apparatus capable of suppressing a phase-contrast image from becoming difficult to see due to a gradation that occurred in the phase-contrast image.

In order to achieve the above-described object, an X-ray phase imaging method according to one aspect of the present invention includes: a step of acquiring a plurality of images while relatively translating a subject and an imaging system composed of an X-ray source, a detector configured to detect X-rays emitted from the X-ray source, and a plurality of gratings arranged between the X-ray source and the detector; a step of generating a phase-contrast image based on the plurality of images; and a step of correcting a gradation that occurred along an orthogonal direction to a translation direction as viewed from an optical axis direction of the X-rays in the phase-contrast image based on a distribution state of the gradation.

According to the present invention, as described above, a phase-contrast image is generated based on a plurality of images acquired with a subject and an imaging system being relatively translated with each other by a moving mechanism, and a gradation that occurred along an orthogonal direction to the translation direction as viewed from the optical axis direction of the X-rays in the phase-contrast image is corrected based on the distribution state of the gradation. With this, it is possible to remove the gradation that occurred along the orthogonal direction to the translation direction as viewed from the optical axis direction of the X-rays in the phase-contrast image. Therefore, it is possible to suppress the phase-contrast image from becoming difficult to see due to the gradation that occurred in the phase-contrast image.

DESCRIPTION OF THE PREFERRED EMBODIMENT

Hereinafter, an embodiment in which the present invention is embodied will be described with reference to the attached drawings.

Referring to FIG. 1 to FIG. 17, the configuration of an X-ray phase imaging apparatus 100 according to an embodiment of the present invention will be described.
Configuration of X-Ray Phase Imaging Apparatus First, referring to FIG. 1, the configuration of the X-ray phase imaging apparatus 100 according to this embodiment will be described.

Figure 1:
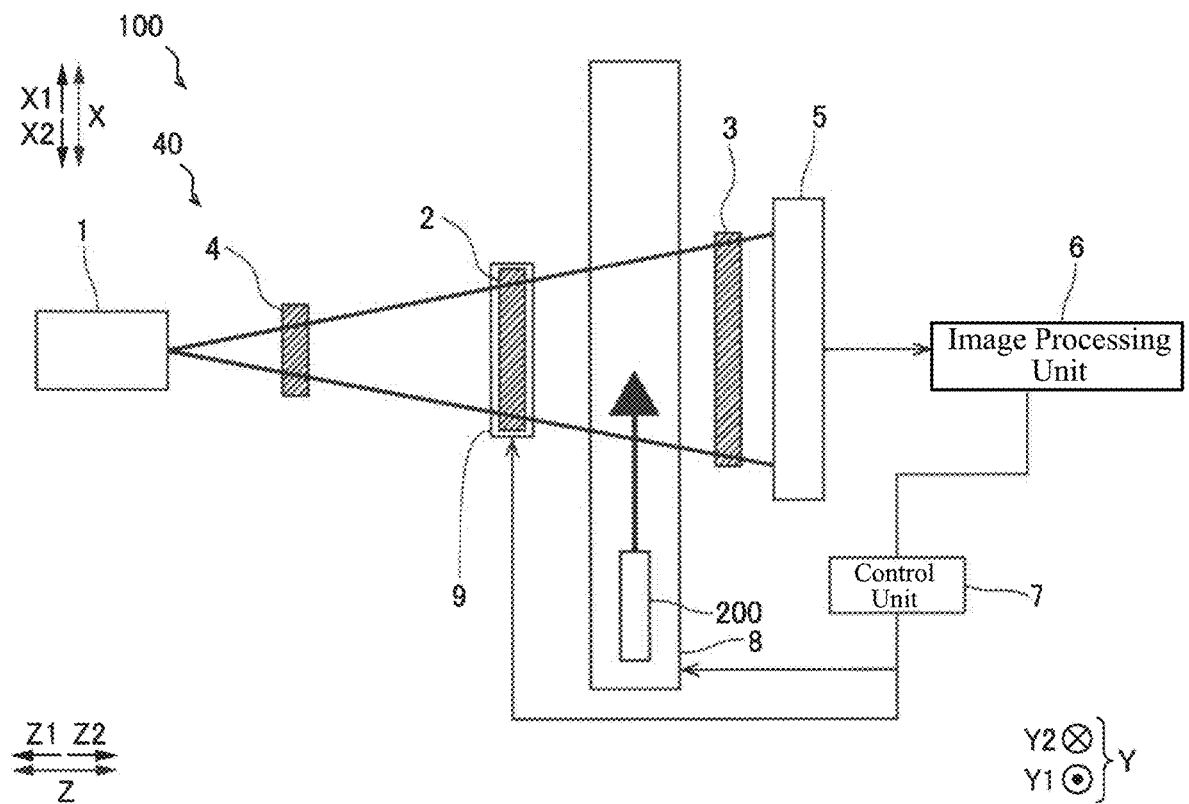
FIG. 1 is a schematic diagram showing the entire configuration of an X-ray phase imaging apparatus according to an embodiment.

As shown in FIG. 1, the X-ray phase imaging apparatus 100 is a device for imaging an inside of a subject 200 by utilizing a Talbot effect. The X-ray phase imaging apparatus 100 can be used for imaging the inside of the subject 200 as an object, for example, in non-destructive inspection applications.

FIG. 1 is a schematic diagram of the X-ray phase imaging apparatus 100 as viewed from the Y-direction. As shown in FIG. 1, the X-ray phase imaging apparatus 100 is provided with an X-ray source 1, a plurality (three) of gratings 2 to 4, a detector 5, an image processing unit 6, a control unit 7, a moving mechanism 8, and a grating moving mechanism 9.

Note that, in this specification, the direction parallel to the optical axis direction of the X-rays is defined as a Z-direction. Of the Z-direction, the direction from the X-ray source 1 to the detector 5 is defined as a Z2-direction, the opposite direction thereof is defined as a Z1-direction. Further, the up-down direction in the plane orthogonal to the Z-direction is defined as an X-direction. Of the X-direction, the upward direction is defined as an X1-direction and the downward direction is defined as an X2-direction. Further, the right-left direction in the plane orthogonal to the Z-direction is defined as a Y-direction. Of the Y-direction, the direction toward the back of the paper surface in FIG. 1 is defined as a Y2-direction, and the direction toward the front side of the paper surface in FIG. 1 is defined as a Y1-direction.

The X-ray source 1 is configured to generate X-rays when a high voltage is applied. The X-ray source 1 is configured to emit the generated X-rays in the Z2-direction.

The grating 2 is arranged between the X-ray source 1 and the grating 3 and is irradiated with the X-rays from the X-ray source 1. The grating 2 is provided to form a self-image of the grating 2 by a Talbot effect. When coherent X-rays pass through a grating in which slits are formed, an image (self-image) of the grating is formed at a predetermined distance (Talbot distance) from the grating. This is called a Talbot effect.

The grating 3 is arranged between the grating 2 and the detector 5 and is irradiated with the X-rays passed through the grating 2. The grating 3 is positioned at a distance of a Talbot distance away from the grating 2. The grating 3 interferes with the self-image of the grating 2 to form a Moire fringe 30 (see FIG. 4).

The grating 4 is arranged between the X-ray source 1 and the grating 2 and is irradiated with the X-rays from the X-ray source 1.

The detector 5 is configured to detect X-rays, convert the detected X-rays into an electric signal, and read the converted electric signal as an image signal. The detector 5 is, for example, an FPD (Flat Panel Detector). The detector 5 includes a plurality of conversion elements (not shown) and pixel electrodes (not shown) arranged on the plurality of conversion elements. The plurality of conversion elements and the plurality of pixel electrodes are arranged in arrays in the X-direction and Y-direction at a predetermined period (pixel pitch). The detector 5 is configured to output the acquired image signal to the image processing unit 6.

The image processing unit 6 is configured to generate a phase-contrast image 16 (see FIG. 7) based on the image signal output from the detector 5. The image processing unit 6 includes processors, such as, e.g., a GPU (Graphics Processing Unit) and an FPGA (Field-Programmable Gate Array) configured for image processing.

The control unit 7 is configured to control the moving mechanism 8 to translate the subject 200 in the X-direction (translation direction). Further, the control unit 7 is configured to control the grating moving mechanism 9 to move the grating 2. Further, the control unit 7 is configured to adjust the position of the grating 2 by controlling the grating moving mechanism 9 to thereby generate a Moire fringe 30 (see FIG. 4) on the detection surface of the detector 5. The control unit 7 includes, for example, a CPU (Central Processing Unit), a ROM (Read Only Memory), and a RAM (Random Access Memory).

The moving mechanism 8 is configured to relatively translate the subject 200 and the imaging system 40 composed of the X-ray source 1, the detector 5, and the plurality of gratings 2 to 4 along the X-direction under the control of the control unit 7. In the example shown in FIG. 1, the moving mechanism 8 is configured to translate the subject 200 along the X-direction. Note that when translating the subject 200 by the moving mechanism 8, the imaging system 40 is fixed. The moving mechanism 8 is configured, for example, by a belt conveyor or various kinds of linear motion mechanisms.

The grating moving mechanism 9 is configured to move the grating 2 under the control of the control unit 7. Further, the grating moving mechanism 9 is configured to generate a Moire fringe 30 (see FIG. 4) by adjusting the position of the grating 2 under the control of the control unit 7. The detailed configuration in which the grating moving mechanism 9 moves the grating will be described later. Further, the grating moving mechanism 9 is holding the grating 2.

Structure of Each Grating

Next, referring to FIG. 2, the structures of the plurality of gratings 2 to 4 will be described.

Figure 2:
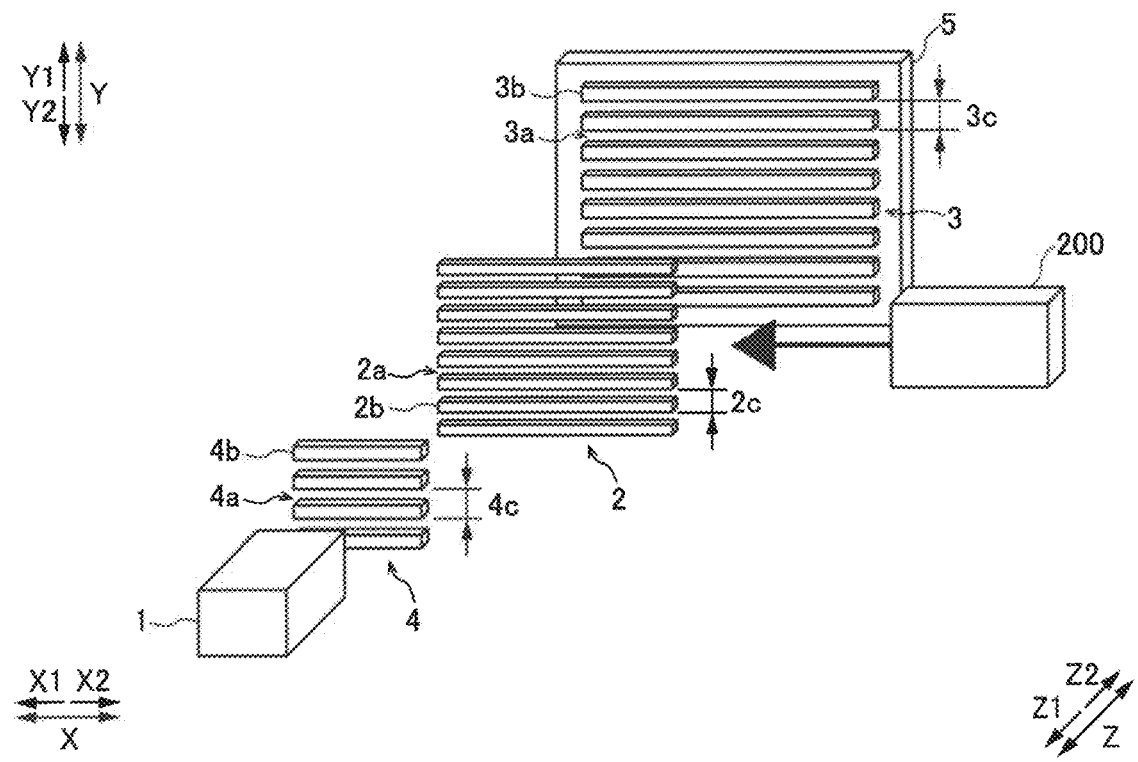
FIG. 2 is a schematic diagram for explaining the arrangement and the construction of a plurality of gratings in an X-ray phase imaging apparatus according to an embodiment.

As shown in FIG. 2, the grating 2 has a plurality of slits 2a and a plurality of X-ray phase change units 2b. Each slit 2a and each X-ray phase change unit 2b are arranged at a predetermined period (pitch) 2c in the Y-direction. The slit 2a and the X-ray phase change unit 2b are each formed to extend linearly. Further, the slit 2a and the X-ray phase change unit 2b are each formed to extend parallel with each other. The grating 2 is a so-called phase grating. Further, the grating 2 is formed in a flat plate shape.

The grating 3 has a plurality of X-ray transmission portions 3a and a plurality of X-ray absorption portions 3b. The X-ray transmission portion 3a and the X-ray absorption portion 3b are arranged in a Y-direction at a predetermined period (pitch) 3c. The X-ray transmission portion 3a and the X-ray absorption portion 3b are each formed to extend linearly. The X-ray transmission portion 3a and the X-ray absorption portion 3b are formed to extend parallel with each other. The grating 3 is a so-called absorption grating. Further, the grating 3 is formed in a flat plate shape. Although the grating 2 and the grating 3 are gratings having different roles, respectively, the slit 2a and the X-ray transmission portion 3a transmit X-rays. The X-ray absorption portion 3b shields X-rays. Further, the X-ray phase change unit 2b changes the phase of the X-rays by the difference of the refractive index between the X-ray phase change unit and the slit 2a.

The grating 4 has a plurality of slits 4a and a plurality of X-ray absorption portions 4b arranged at a predetermined period (pitch) 4c in the Y-direction. The slit 4a and the X-ray absorption portion 4b are each formed to extend linearly. The slit 4a and the X-ray absorption portion 4b are formed to extend in parallel with each other. Further, the grating 4 is configured to make the X-rays passed through each slit 4a act as a line light source corresponding to the position of each slit 4a. Further, the grating 4 is formed in a flat plate shape.

Grating Moving Mechanism

Next, referring to FIG. 3, the structure of the grating moving mechanism 9 will be described.

Figure 3:
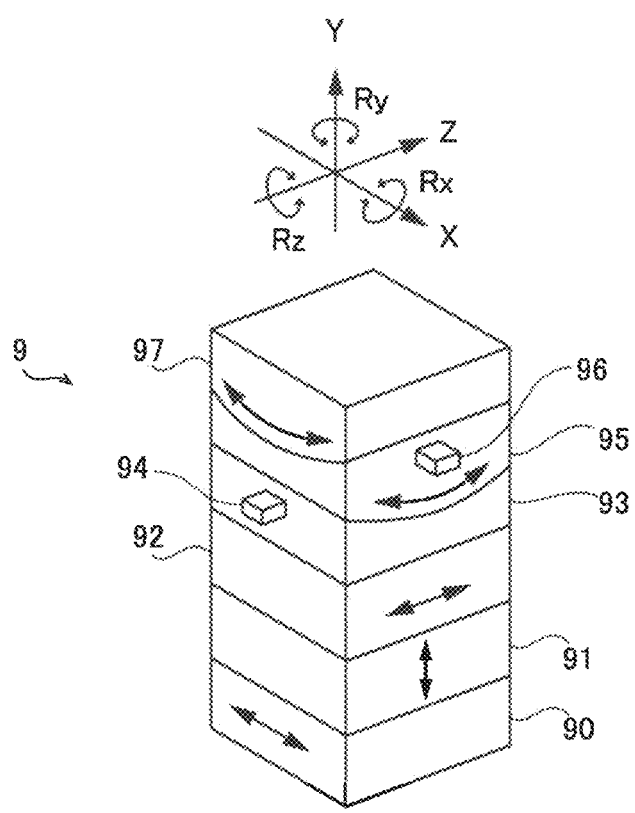
FIG. 3 is a schematic diagram for explaining the configuration of a grating position adjustment mechanism according to an embodiment.

As shown in FIG. 3, the grating moving mechanism 9 is configured to move the grating 2 in the X-direction, the Y-direction, the Z-direction, the rotation direction Rz around the axis extending in the Z-direction, the rotation direction Rx around the axis extending in the X-direction, and the rotation direction Ry around the axis extending in the Y-direction. Specifically, the grating moving mechanism 9 includes an X-direction linear motion mechanism 90, a Y-direction linear motion mechanism 91, a Z-direction linear motion mechanism 92, a linear motion mechanism connection unit 93, a stage support unit drive unit 94, a stage support unit 95, a stage drive unit 96, and a stage 97. The X-direction linear motion mechanism 90 is configured to be movable in the X-direction. The X-direction linear motion mechanism 90 includes, for example, a motor or the like. The Y-direction linear motion mechanism 91 is configured to be movable in the Y-direction. The Y-direction linear motion mechanism 91 includes, for example, a motor and the like. The Z-direction linear motion mechanism 92 is configured to be movable in the Z-direction. The Z-direction linear motion mechanism 92 includes, for example, a motor or the like.

The grating moving mechanism 9 is configured to move the grating 2 in the X-direction by the operation of the X-direction linear motion mechanism 90. Further, the grating moving mechanism 9 is configured to move the grating 2 in the Y-direction by the operation of the Y-direction linear motion mechanism 91. Further, the grating moving mechanism 9 is configured to move the grating 2 in the Z-direction by the operation of the Z-direction linear motion mechanism 92.

The stage support unit 95 supports the stage 97 in the up-down direction (Y1-direction). The stage drive unit 96 is configured to reciprocate the stage 97 in the X-direction direction. The stage 97 is formed so that the bottom has a convex curved shape toward the stage support unit 95 and is configured to be rotated about the axis extending in the Z-direction (Rz-direction) by being reciprocated in the X-direction. Further, the stage support unit drive unit 94 is configured to reciprocate the stage support unit 95 in the Z-direction. Further, the stage support unit 95 is formed so that the bottom portion has a convex curved shape toward the linear motion mechanism connecting unit 93 and is configured to be rotated about the axis extending in the X-direction (Rx-direction) by being reciprocated in the Z-direction. Further, the linear motion mechanism connection unit 93 is provided to the X-direction linear motion mechanism 90 to be rotatable about the axis extending in the Y-direction (Ry direction). Thus, the grating moving mechanism 9 can rotate the grating 2 about the central axis extending in the Y-direction.

Generation of Phase-Contrast Image

Next, referring to FIG. 4 to FIG. 7, the configuration in which the X-ray phase imaging apparatus 100 according to this embodiment generates a phase-contrast image 16 (see FIG. 7) will be described.

In this embodiment, the X-ray phase imaging apparatus 100 is configured to image the subject 200 while relatively translating the subject 200 and the imaging system 40 in the X-direction (translation direction) by the moving mechanism 8. Further, the X-ray phase imaging apparatus 100 is configured to image the subject 200 in a state in which the Moire fringe 30 is generated in advance.

Figure 4:
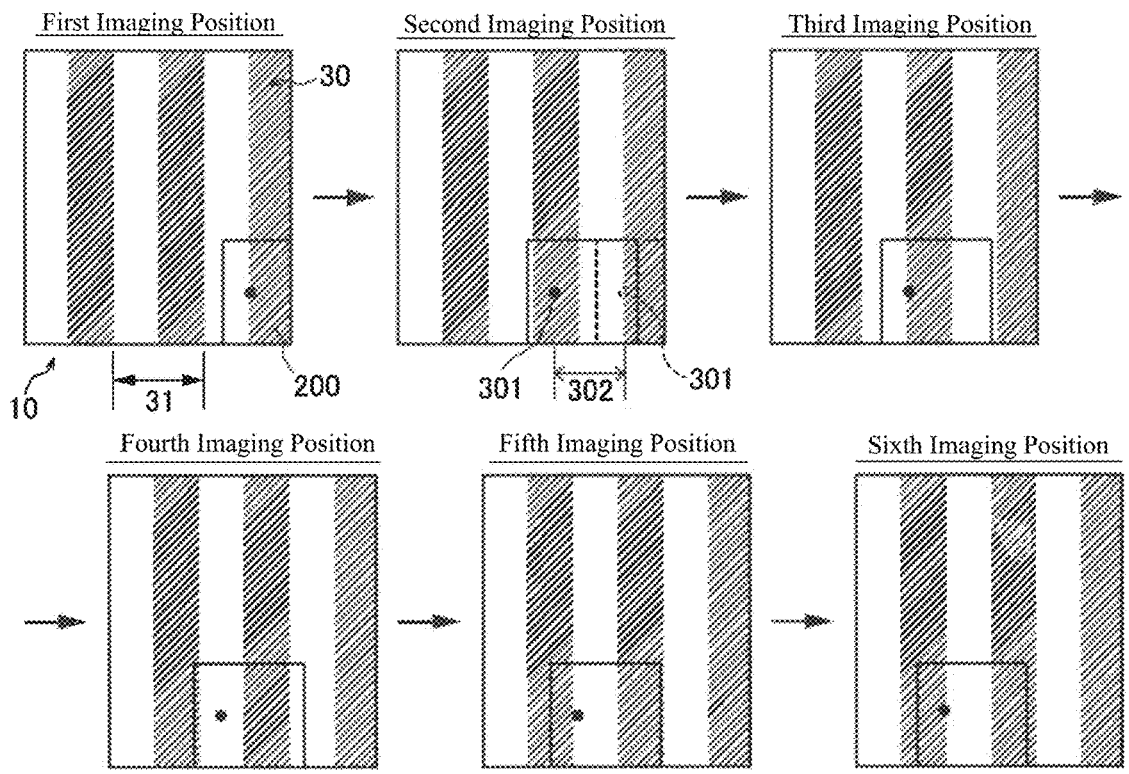
FIG. 4 is a schematic diagram showing a plurality of images acquired by an X-ray phase imaging apparatus according to an embodiment.

FIG. 4 is a schematic diagram of a plurality of subject images 10 captured while translating the subject 200 in the X-direction at six imaging positions of the first imaging position to the sixth imaging position by the moving mechanism 8. That is, the plurality of subject images 10 shown in FIG. 4 is acquired by repeating moving the subject 200 to each imaging position and imaging the subject 200 with the subject stopped. Specifically, the example shown in FIG. 4 is an example in which imaging is performed at each position of six positions during which the subject 200 of a rectangular shape is moved from one side (right side) of the imaging range to the other side thereof (left side).

Note that the example shown in FIG. 4 is an example in which a part of the subject 200 is not reflected in the subject image 10 since the part of the subject 200 is not arranged on the detection surface of the detector 5 at the first imaging position in the X-direction. Further, the example shown in FIG. 4 is an example showing the change in the position of the pixel 301 among the pixels representing the subject 200 in the plurality of subject images 10. Further, the plurality of subject images 10 is an example of "a plurality of images acquired while relatively translating a subject and an imaging system" recited in claims.

As shown in FIG. 4, in this embodiment, the control unit 7 is configured to image the subject 200 while translating the subject 200 in the X-direction in a state in which a Moire fringe 30 is generated. The control unit 7 moves the subject 200 by a predetermined movement amount 302 by inputting a command value related to a travel amount for arranging the subject 200 at each imaging position to the moving mechanism 8. The command value related to the travel amount is, for example, the number of pulses input to the moving mechanism 8 when the moving mechanism 8 includes a stepping motor as a drive source.

Note that in the subject image 10 at the second imaging position shown in FIG. 4, in order to facilitate grasping of the travel amount 302 of the subject 200, the position of the subject 200 in the first imaging position is illustrated by a broken line. By imaging while translating the subject 200 in the X-direction by the moving mechanism 8, it is possible to relatively move the Moire fringe 30 and the subject 200, so that the image processing unit 6 can generate a phase-contrast image 16 (see FIG. 7). Note that in this embodiment, the subject 200 is moved by at least one cycle 31 or more of the Moire fringe 30 by the moving mechanism 8.

Here, in a conventional fringe scanning method, imaging is performed by translating a grating by a predetermined distance acquired by dividing one period of the grating for at least a vertical component in the grating direction. Therefore, since the phase value of the Moire fringe 30 of each pixel in each image is determined by the distance that the grating is moved, a phase-contrast image 16 can be generated by acquiring the pixel value of the pixel in each image.

Figure 5:
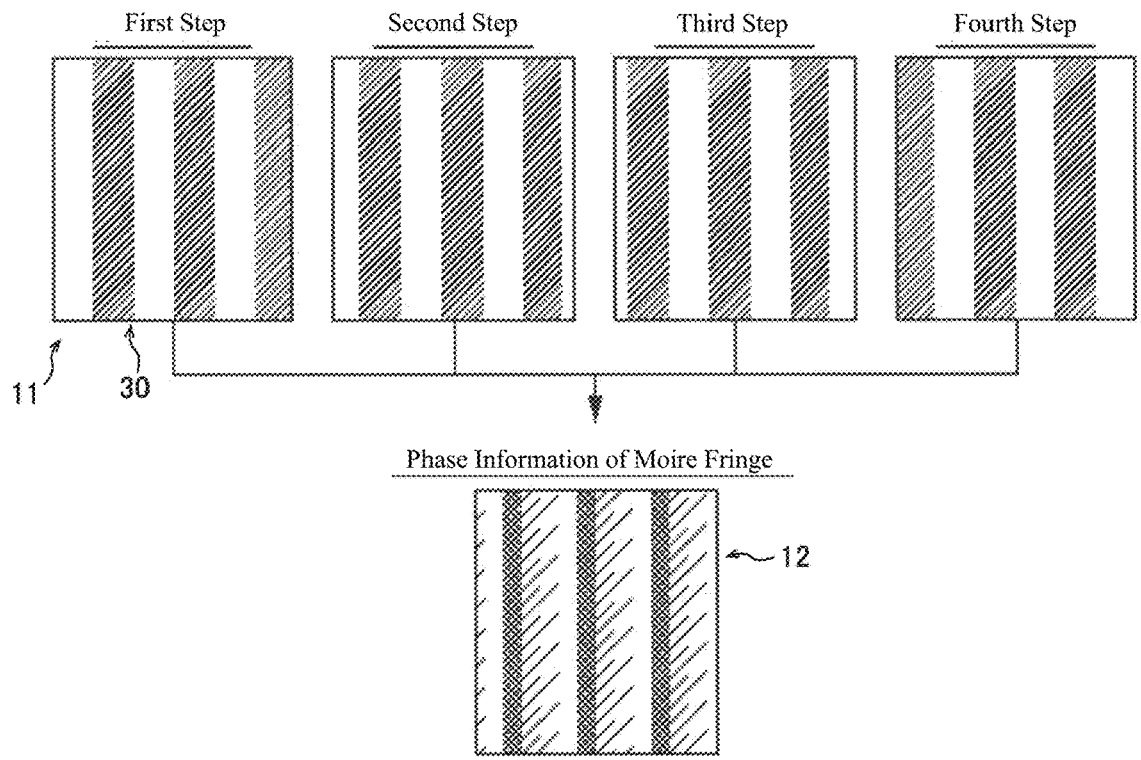
FIG. 5 is a schematic diagram for explaining the configuration for acquiring phase information of a Moire fringe acquired by an X-ray phase imaging apparatus according to an embodiment.

However, in the case of performing the imaging while moving the subject 200 with respect to the Moire fringe 30, it is not possible to directly acquire the phase value of the pixel in each image. Therefore, in this embodiment, the image processing unit 6 is configured to acquire the phase information 12 of the Moire fringe 30 (see FIG. 5). Specifically, the X-ray phase imaging apparatus 100 acquires the Moire fringe image 11 of each Step as shown in FIG. 5 by translating the grating 2 by the grating moving mechanism 9. The Moire fringe image 11 is an image acquired by imaging the Moire fringe 30 generated on the detection surface of the detector 5 by translating the grating 2 and is an image acquired by capturing the image of the fringe pattern due to the light and darkness of the pixel value of the Moire fringe 30.

The image processing unit 6 is configured to acquire the phase information 12 of the Moire fringe 30 based on each Moire fringe image 11. Specifically, the Moire fringe image 11 in the first step to the fourth step of FIG. 5 is defined as $I_k(x, y)$, and $S(x, y)$ is defined as shown in the following equation (1).

$$S(x, y) = \sum_{k=1}^{M} I_k(x, y) \exp\left(-\frac{2i\pi k}{M}\right) \quad (1)$$

Where "k" is the number of each Step. "M" is the number of times that the grating is translated. Further, "x" and "y" are pixel positions (coordinates) in the plane orthogonal to the irradiation axis of the X-rays on the detection plane of the detector 5.

Using the above-described equation (1), the phase information 12 of the Moire fringe 30 is represented by the following equation (2).

$$\varphi(x,y) = \arg[S(x,y)] \quad (2)$$

Here, $\varphi(x, y)$ is the phase information 12 of the Moire fringe 30. In this embodiment, considering $I_k(X, y)$ as a function of k, fitting may be performed by a sine curve to acquire the phase information of the sign curve as phase information 12 of the Moire fringe 30.

The phase information 12 of the Moire fringe 30 is an image of a fringe pattern in which the change of the phase value of the Moire fringe 30 is repeated every one cycle 31. Specifically, the phase information 12 of the Moire fringe 30 is an image in which the change of the phase value of the Moire fringe 30 from $-\pi$ to $\pi$ is illustrated in a fringe pattern. The phase information 12 of the Moire fringe 30 may be an image in the range of $-\pi$ to $\pi$ or an image in the range of 0 to 2n, provided that the range of acquiring the change of the phase value is $2\pi$.

In this embodiment, the image processing unit 6 is configured to associate the pixel value of each pixel of the subject 200 in the plurality of subject images 10 with the phase value of the Moire fringe 30 in each pixel based on the plurality of subject images 10 acquired while relatively translating the subject 200 and the imaging system 40 and the phase information 12 of the Moire fringe 30 generated in the plurality of subject images 10.

Figure 6:
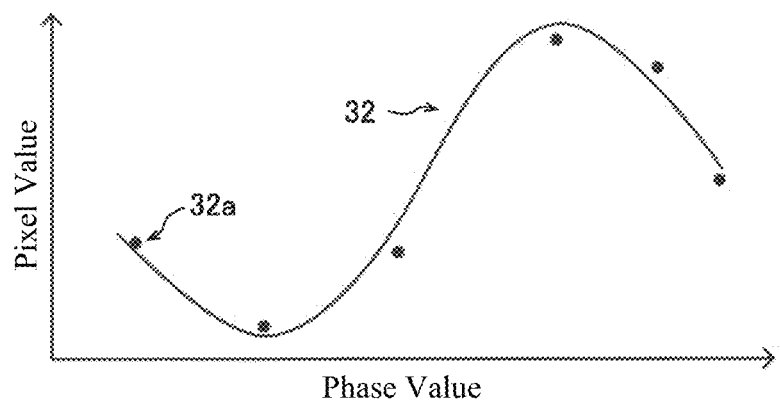
FIG. 6 is a schematic diagram showing an intensity signal curve acquired by associating each phase value and each pixel value of each pixel of a plurality of images according to an embodiment in a one-to-one relation.

Further, as shown in FIG. 6, the image processing unit 6 is configured to acquire the intensity signal curve 32 (see FIG. 10) indicating the relationship between the phase value and the pixel value for the pixels in each subject image 10. In the graph showing the intensity signal curve 32 shown in FIG. 6, the horizontal axis indicates the phase value, and the vertical axis indicates the pixel value. The image processing unit 6 is configured to acquire the intensity signal curve 32 of the pixel values in which each phase value and each pixel value of the pixel of the same position of the subject 200 in the plurality of subject images 10 are associated with each other in a one-to-one relationship using each subject image 10 and the phase information 12.

The example shown in FIG. 6 is an example of the intensity signal curve 32 acquired by acquiring plots 32a based on a pixel value at each pixel 301 of the plurality of subject images 10 and a phase value of each point corresponding to the pixel 301 of the subject image 10 in the plurality of phase information 12 and fitting by a sine wave. The image processing unit 6 is configured to generate the phase-contrast image 16 based on the acquired intensity signal curve 32.

Figure 7:
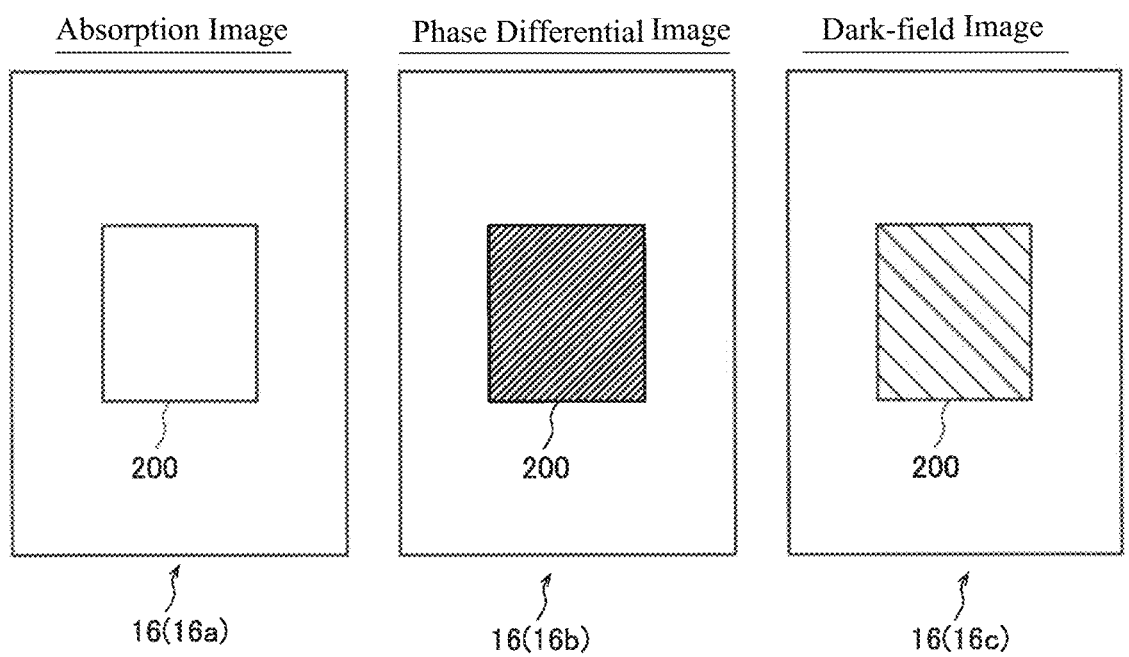
FIG. 7 is a schematic diagram showing a phase-contrast image generated by an image processing unit according to an embodiment.

FIG. 7 is a schematic diagram of phase-contrast images 16. In this embodiment, the image processing unit 6 is configured to generate the phase-contrast image 16 based on the intensity signal curve 32. The phase-contrast image 16 includes an absorbing image 16a, a phase differential image 16b, and a dark-field image 16c. The method of generating the absorbing image 16a, the phase differential image 16b, and the dark-field image 16c can be performed by known methods, and therefore the explanation thereof is omitted.

Note that the absorption image 16a is an image of the contrast caused by the difference in the X-ray absorption due to the subject 200. The phase differential image 16b is an image of the contrast caused by the change in the phase of the X-rays due to the subject 200. The dark-field image 16c is an image of the contrast caused by the refraction (scattering) of the X-rays due to the microstructures inside the subject 200. In other words, the dark-field image 16c is an image of the reduction in the visibility due to the subject 200, and the reduction in the visibility depends on the degree of scattering of the subject 200. That is, the dark-field image is an image of the X-ray scattering of the subject 200.

Amendment of Gradation

Next, referring to FIG. 8 to FIG. 12, the configuration related to the correction of the gradation 16d that occurred in the phase-contrast image 16 will be described. In FIG. 8 to FIG. 12, for convenience, the gradation 16d is schematically illustrated by hatching.

Figure 8:
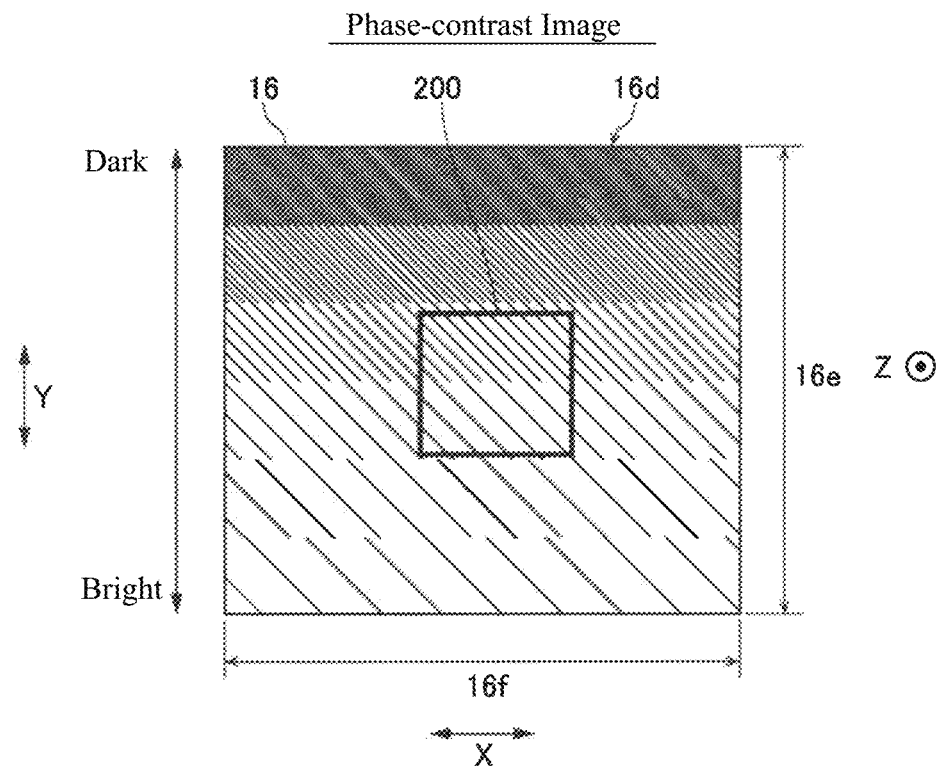
FIG. 8 is a schematic diagram for explaining a gradation that occurred in a phase-contrast image generated by an image processing unit according to an embodiment.

In this embodiment, as shown in FIG. 8, the image processing unit 6 is configured to correct the gradation 16d that occurred along the orthogonal direction (Y-direction) to the translation direction (X-direction) as viewed from the optical axis direction (Z-direction) of the X-rays in the phase-contrast image 16 based on the distribution state of the gradation 16d. Specifically, the image processing unit 6 is configured to correct the gradation 16d so that the gradation 16d becomes flat based on the distribution state of the gradation 16d.

The gradation 16d is formed throughout the phase-contrast image 16. Further, the gradation 16d is formed so that the light and shade (light-dark) continuously changes along the Y-direction. Specifically, the gradation 16d shown in FIG. 8 is formed to be gradually brighter from one side in the Y-direction toward the other side thereof. The gradation 16d is formed in a stripe shape extending along the X-direction.

Note that the gradation 16d occurs along the Y-direction regardless of the orientation of the gratings 2 to 4. That is, when the gratings 2 to 4 are arranged along the Y-direction as shown in FIG. 2, when the gratings 2 to 4 are arranged along the X-direction unlike the configuration shown in FIG. 2, and when the gratings 2 to 4 are arranged inclined with respect to the X-direction and the Y-direction, the gradation 16d occurs along the Y-direction.

Figure 9:
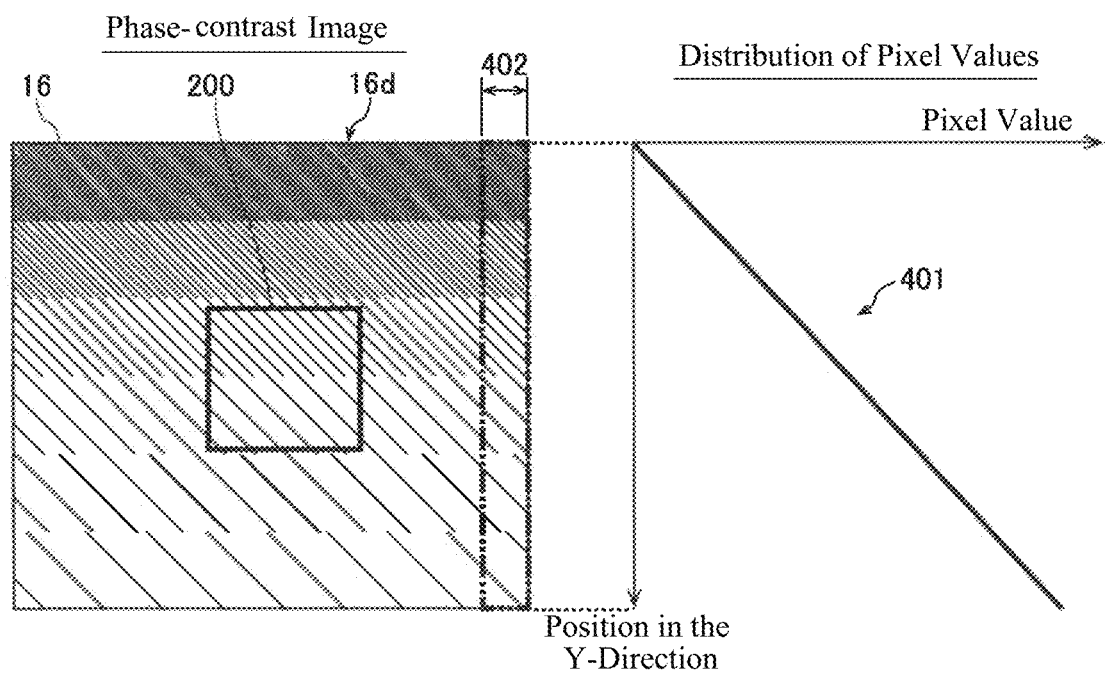
FIG. 9 is a schematic diagram for explaining the distribution of pixel values of a phase-contrast image acquired by an image processing unit according to an embodiment.

As shown in FIG. 9, the image processing unit 6 is configured to acquire the distribution 401 of the pixel values (e.g., the brightness value) along the Y-direction of the phase-contrast image 16 and correct the gradation 16d based on the distribution 401 of the acquired pixel values. Specifically, the image processing unit 6 is configured to correct the gradation 16d based on the distribution 401 of the pixel values ranging from one end of the phase-contrast image 16 in the Y-direction to the other end thereof. That is, the image processing unit 6 is configured to correct the gradation 16d based on the distribution 401 of the pixel values ranging in the width 16e of the phase-contrast image 16 in the Y-direction (see FIG. 8). Note that in FIG. 9, the range of acquiring the distribution 401 of the pixel values is schematically illustrated by the two-dot chain line.

The image processing unit 6 is configured to acquire the distribution 401 of the pixel values in the region of the phase-contrast image 16 in which there exists no subject 200. That is, the image processing unit 6 is configured to correct the gradation 16d based on the distribution 401 of the pixel values in the region of the phase-contrast image 16 where there exists no subject 200. The image processing unit 6 is configured to acquire the distribution 401 of the pixel values in the vicinity of the end of the phase-contrast image 16 in the X-direction. That is, the image processing unit 6 is configured to correct the gradation 16d based on the distribution 401 of the pixel values in the vicinity of the end of the phase-contrast image 16 in the X-direction.

Further, the distribution 401 of the pixel values is the distribution of the average pixel values of the pixel group having the predetermined width 402 in the X-direction. Specifically, the distribution 401 of the pixel values is the distribution of the average pixel values of the pixel group having the predetermined width 402 in the X-direction from one end of the phase-contrast image 16 in the Y-direction to the other end thereof. The predetermined width 402 is not particularly limited but may be, for example, a width of about 50 pixels.

Figure 10:
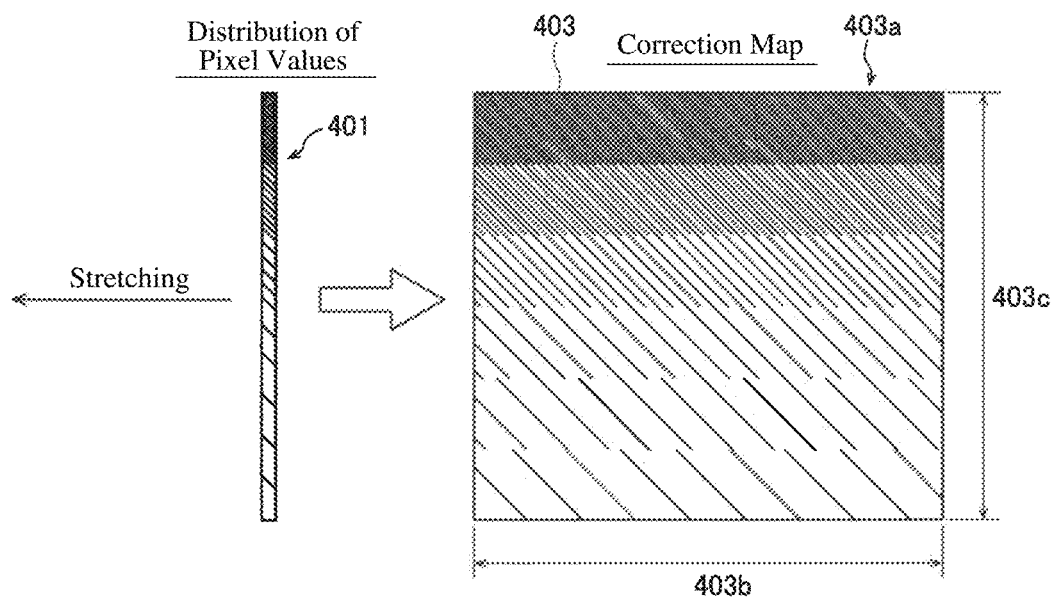
FIG. 10 is a schematic diagram for explaining a correction map of a phase-contrast image generated by an image processing unit according to an embodiment.
Figure 11:
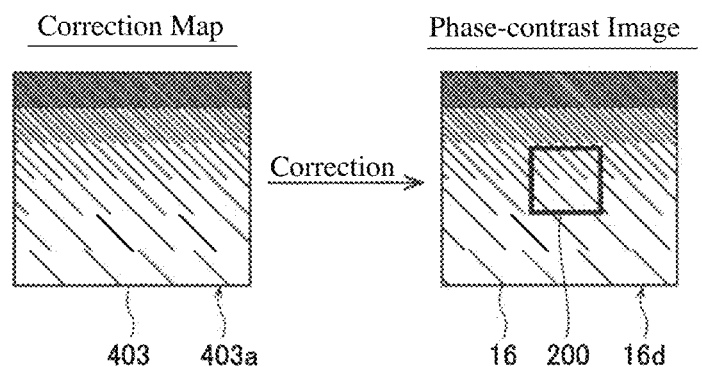
FIG. 11 is a schematic diagram for explaining a configuration for correcting a phase-contrast image with a correction map by an image processing unit according to one embodiment.

Further, as shown in FIG. 10 and FIG. 11, the image processing unit 6 is configured to generate a correction map 403 by stretching the distribution 401 of the pixel values in the X-direction. The correction map 403 is a gradation map including a gradation 403a corresponding to the gradation 16d of the phase-contrast image 16. The image processing unit 6 is configured to correct the gradation 16d based on the generated correction map 403.

Specifically, the image processing unit 6 is configured to generate the correction map 403 by stretching the distribution 401 of the pixel values in the X-direction so as to have the same number of pixels as the number of pixels of the phase-contrast image 16 in the X-direction, and correct the gradation 16d based on the generated correction map 403.

For example, when the number of pixels of the phase-contrast image 16 in the X-direction is 1,000 pixels, the image processing unit 6 generates the correction map 403 by stretching the distribution 401 of the pixel values in the X-direction so that the number of pixels in the X-direction becomes 1,000 pixels. This produces the correction map 403 in which the number of pixels in the X-direction is the same as that of the phase-contrast image 16 and the number of pixels in the Y-direction is the same as that of the phase-contrast image 16. The width 403b of the correction map 403 in the X-direction is the same size (number of pixels) as the width 16f of the phase-contrast image 16 in the X-direction (see FIG. 8). Further, the width 403c of the correction map 403 in the Y-direction is equal to the same size (number of pixels) as the width 16e of the phase-contrast image 16 in the Y-direction.

The image processing unit 6 is configured to correct the gradation 16d by dividing the phase-contrast image 16 by the correction map 403 or subtracting the correction map 403 from the phase-contrast image 16. Specifically, the image processing unit 6 is configured to correct the gradation 16d by dividing the pixel value of the pixel of the phase-contrast image 16 by the pixel value of the corresponding pixel of the correction map 403, or by subtracting the pixel value of the corresponding pixel of the correction map 403 from the pixel value of the pixel of the phase-contrast image 16.

Figure 12:
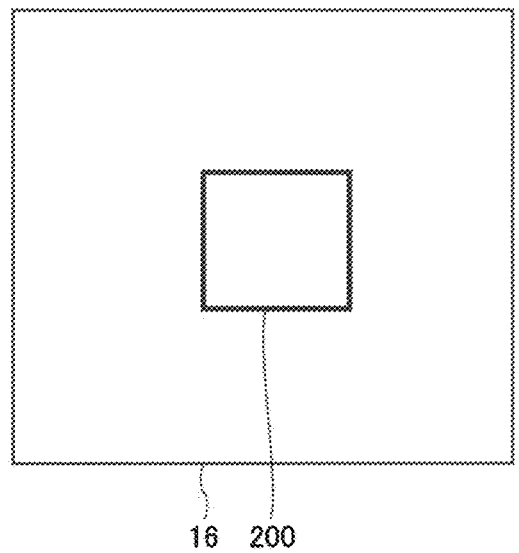
FIG. 12 is a schematic diagram for explaining a phase-contrast image corrected by an image processing unit according to an embodiment.

With this, as shown in FIG. 12, the phase-contrast image 16 from which the gradation 16d has been removed can be acquired.

Next, referring to FIG. 13 to FIG. 17, the configuration will be described in which the gradation 17a is corrected in the phase-contrast image 17 in which a plurality of phase-contrast images 16 is joined together. In FIG. 13 to FIG. 17, for convenience, the gradation 17a is schematically illustrated by hatching.

Figure 13:
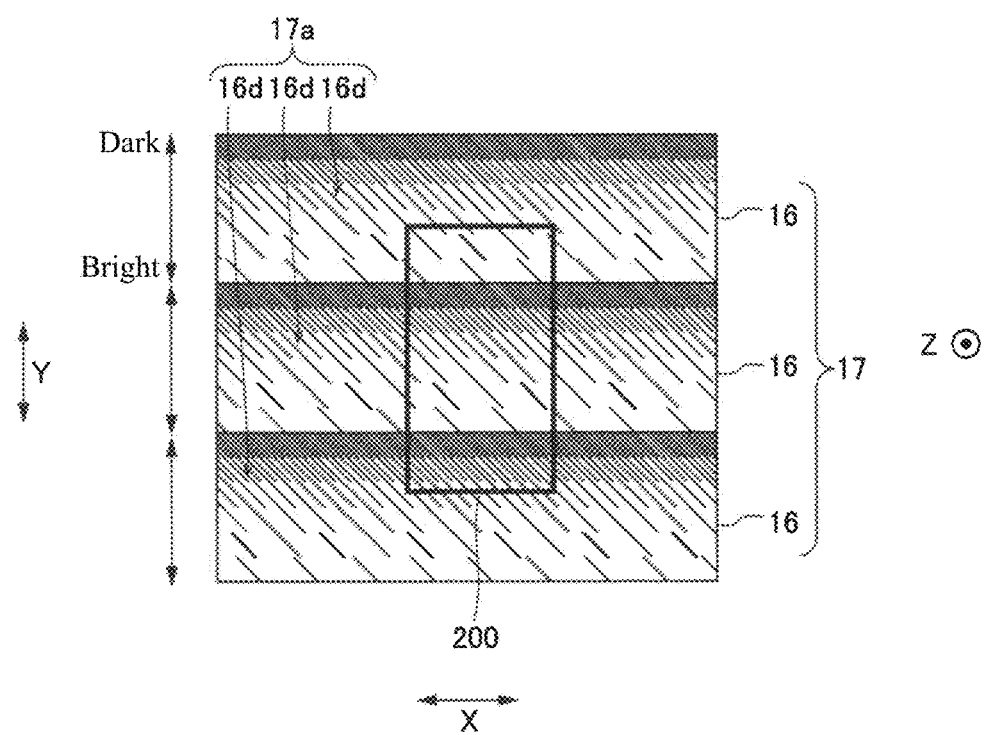
FIG. 13 is a schematic diagram for explaining a gradation that occurred in a phase-contrast image acquired by joining a plurality of phase-contrast images generated by an image processing unit according to an embodiment.

In this embodiment, as shown in FIG. 13, the image processing unit 6 is configured to generate a phase-contrast image 17 in which a plurality of phase-contrast images 16 is joined. This allows the entire subject 200 to be accommodated in the phase-contrast image 17 in which a plurality of phase-contrast images 16 is joined together, even in cases where the entire subject 200 does not fit in a single phase-contrast image 16 due to the large subject 200. Note that the plurality of phase-contrast images 16 to be joined is acquired by changing the position between the imaging system 40 and the subject 200 in the Y-direction. Further, in the example shown in FIG. 13, an example is illustrated in which three phase-contrast images 16 are joined, but a plurality of (other than three) phase-contrast images 16 may be joined.

The phase-contrast image 17 includes a gradation 17*a*. The gradation 17*a* is constituted by gradations 16*d* of the respective phase-contrast images 16.

The correction of the gradation 17*a* in the phase-contrast image 17 is similar to the correction of the gradation 16*d* in the phase-contrast image 16. That is, the image processing unit 6 is configured to correct the gradation 17*a* that occurred in the Y-direction in the phase-contrast image 17 based on the distribution state of the gradation 17*a*. Specifically, the image processing unit 6 is configured to correct the gradation 17*a* so that the gradation 17*a* becomes flat based on the distribution state of the gradation 17*a*.

Figure 14:
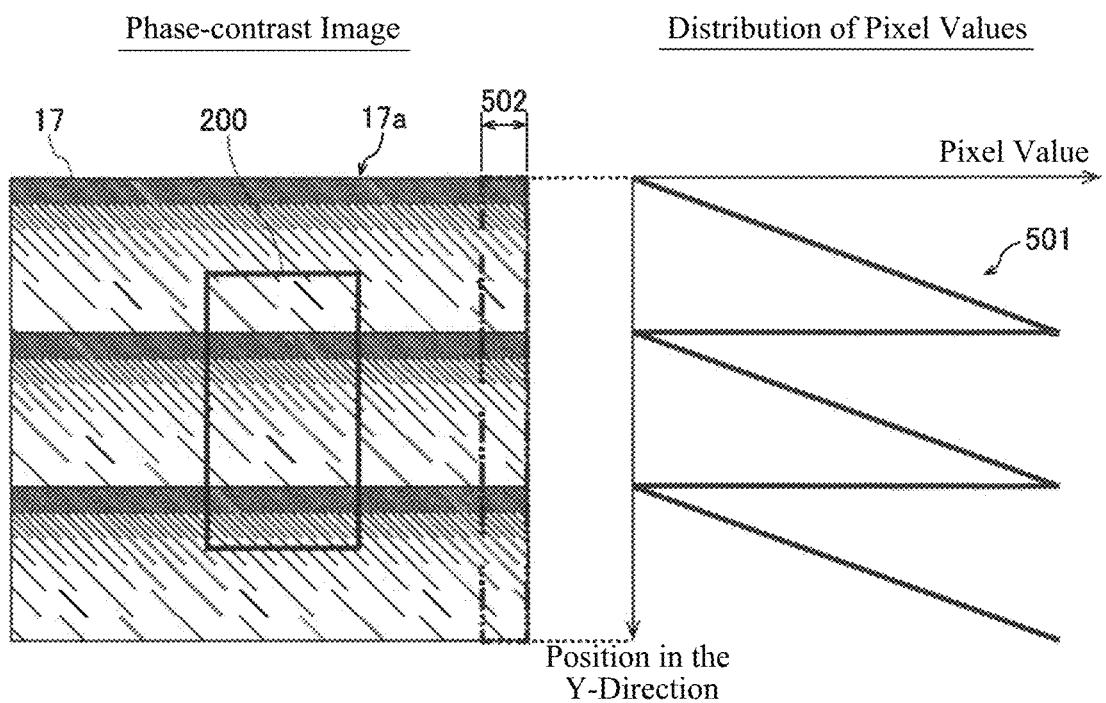
FIG. 14 is a schematic diagram for explaining the distribution of pixel values of a phase-contrast image acquired by joining a plurality of phase-contrast images acquired by an image processing unit according to an embodiment.

As shown in FIG. 14, the image processing unit 6 is configured to acquire the distribution 501 of the pixel values of the phase-contrast image 17 along the Y-direction and correct the gradation 17*a* based on the distribution 501 of the acquired pixel values. Specifically, the image processing unit 6 is configured to correct the gradation 17*a* based on the distribution 501 of the pixel values ranging from one end of the phase-contrast image 17 in the Y-direction to the other end thereof. In FIG. 14, the range of acquiring the distribution 501 of the pixel values is schematically illustrated by a two-dot chain line.

The image processing unit 6 is configured to acquire the distribution 501 of the pixel values in the region of the phase-contrast image 17 in which there exists no subject 200. That is, the image processing unit 6 is configured to correct the gradation 17*a* based on the distribution 501 of the pixel values of the region of the phase-contrast image 17 in which there exists no subject 200. The image processing unit 6 is configured to acquire the distribution 501 of the pixel values in the vicinity of the end of the phase-contrast image 17 in the X-direction. That is, the image processing unit 6 is configured to correct the gradation 17*a* based on the distribution 501 of the pixel values in the vicinity of the end of the phase-contrast image 17 in the X-direction.

Further, the distribution 501 of the pixel values is a distribution of average pixel values of a pixel group having a predetermined width 502 in the X-direction. Specifically, the distribution 501 of the pixel values is a distribution of average pixel values of a pixel group having a predetermined width 502 in X-direction from one end of the phase-contrast image 17 in the Y-direction to the other end thereof. The predetermined width 502 is not particularly limited but may be, for example, a width of about 50 pixels.

Figure 15:
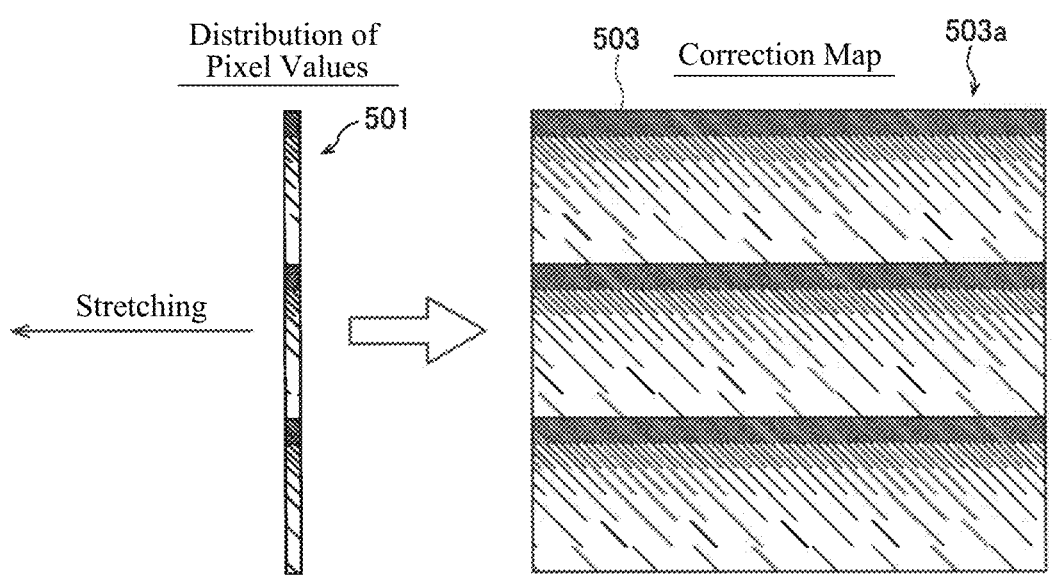
FIG. 15 is a schematic diagram for explaining a correction map of a phase-contrast image acquired by joining a plurality of phase-contrast images generated by an image processing unit according to an embodiment.
Figure 16:
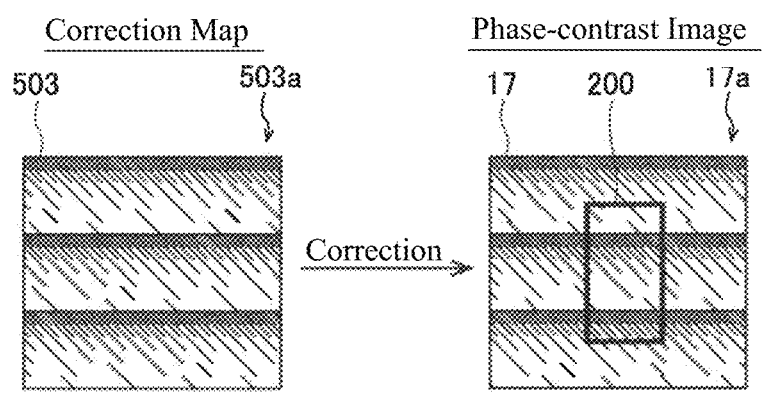
FIG. 16 is a schematic diagram for explaining a configuration for correcting a phase-contrast image acquired by joining a plurality of phase-contrast images with a correction map by an image processing unit according to an embodiment.

Further, as shown in FIG. 15 and FIG. 16, the image processing unit 6 is configured to generate the correction map 503 by stretching the distribution 501 of the pixel values in the X-direction. The correction map 503 is a gradation map including a gradation 503*a* corresponding to the gradation 17*a* of the phase-contrast image 17. The image processing unit 6 is configured to correct the gradation 17*a* based on the generated correction map 503. Specifically, the image processing unit 6 is configured to generate the correction map 503 by stretching the distribution 501 of the pixel values in the X-direction so as to have the same number of pixels as the number of pixels of the phase-contrast image 17 in the X-direction, and to correct the gradation 17*a* based on the generated correction map 503.

Note that it is the same as in the phase-contrast image 16 in that the number of pixels in the X-direction is the same as that of the phase-contrast image 17 and that the correction map 503 in which the number of pixels in the Y-direction is the same as that of the phase-contrast image 17 is generated.

The image processing unit 6 is configured to correct the gradation 17*a* by dividing the phase-contrast image 17 by the correction map 503 or subtracting the correction map 503 from the phase-contrast image 17. Specifically, the image processing unit 6 is configured to correct the gradation 17*a* by dividing the pixel value of the pixel of the phase-contrast image 17 by the pixel value of the corresponding pixel of the correction map 503, or by subtracting the pixel value of the corresponding pixel of the correction map 503 from the pixel value of the pixel of the phase-contrast image 17.

Figure 17:
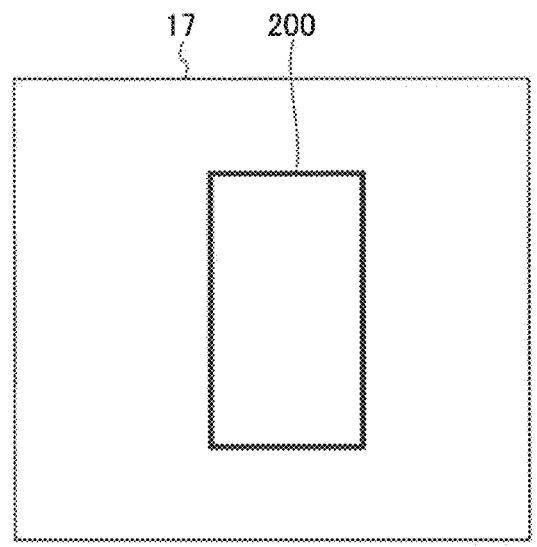
FIG. 17 is a schematic diagram for explaining a phase-contrast image acquired by joining a plurality of phase-contrast images corrected by an image processing unit according to an embodiment.

As a result, as shown in FIG. 17, the phase-contrast image 17 from which the gradation 17*a* has been removed can be acquired.

Next, referring to FIG. 18 to FIG. 20, the gradation 18*a* in the actual phase-contrast image 18, and the correction for this gradation 18*a* will be described. Note that the phase-contrast image 18 is acquired, like the phase-contrast image 17 shown in FIG. 13, by joining three phase-contrast images. Also note that the phase-contrast image 18 is a phase differential image.

Figure 18:
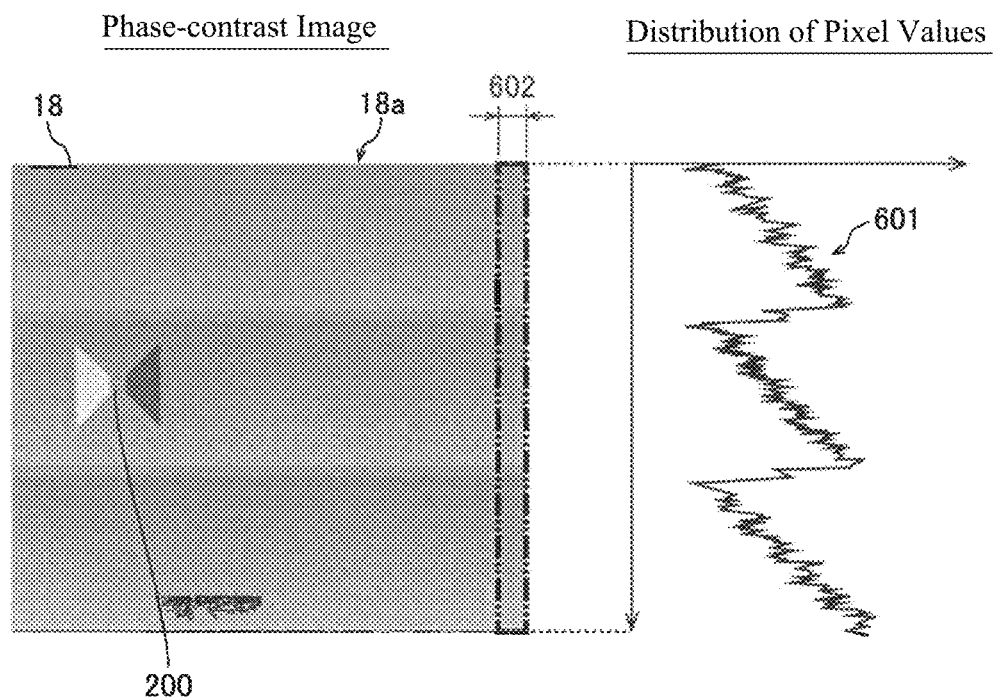
FIG. 18 is a diagram showing an example of an actual phase-contrast image and a diagram illustrating an example of a distribution of pixel values of an actual phase-contrast image.

As shown in FIG. 18, the phase-contrast image 18 includes a gradation 18*a* that occurred along the direction orthogonal to the translation direction as viewed from the optical axis direction of the X-rays. The distribution 601 of the pixel values of this phase-contrast image 18 is as shown in FIG. 18. Note that the distribution 601 of the pixel values is the distribution of the average pixel values of the pixel group having the predetermined width 602 in the X-direction. The predetermined width 602 is 50 pixels.

Figure 19:
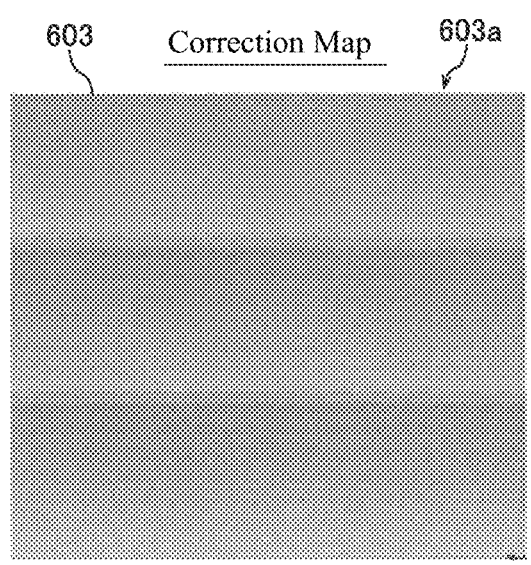
FIG. 19 is a diagram showing a correction map of a phase-contrast image shown in FIG. 18.

As shown in FIG. 19, a correction map 603 was generated by stretching the distribution 601 of the pixel values in the translation direction. The correction map 603 includes a gradation 603*a* corresponding to the gradation 18*a* of the phase-contrast image 18. The correction map 603 has the same size as that of the phase-contrast image 18. Then, the gradation 18*a* was corrected by dividing the phase-contrast image 18 by the correction map 603.

Figure 20:
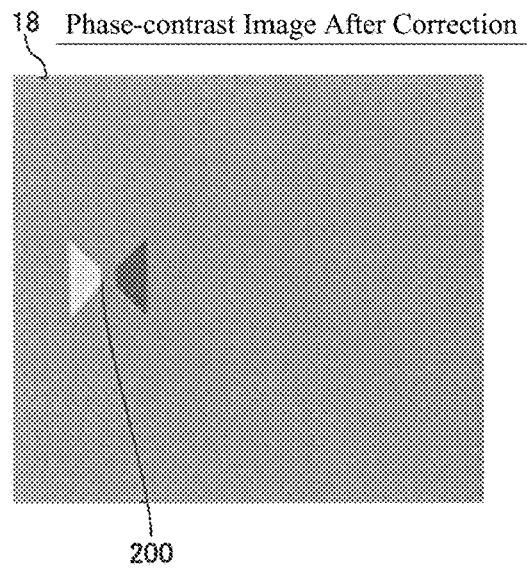
FIG. 20 is a diagram showing a phase-contrast image acquired by correcting the phase-contrast image shown in FIG. 18 by the correction map shown in FIG. 19.

As a result, as shown in FIG. 20, a phase-contrast image 18 from which the gradation 18*a* has been removed could be acquired.

Phase-Contrast Image Generation Processing

Next, referring to FIG. 21, the phase-contrast image generation processing according to the X-ray phase imaging apparatus 100 of this embodiment will be described with reference to a flowchart. Note that each processing of the flowchart is performed by the image processing unit 6.

Figure 21:
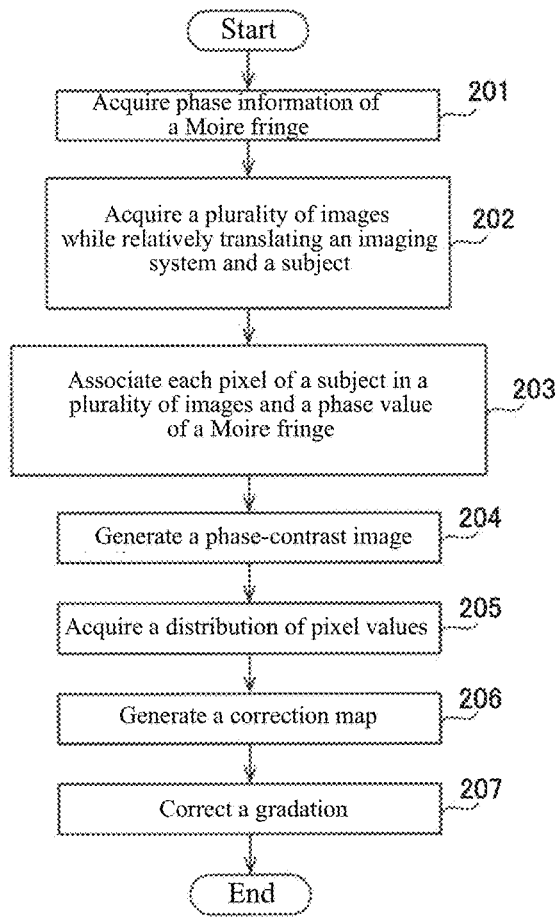
FIG. 21 is a flowchart for explaining phase-contrast image generation processing of an X-ray phase imaging apparatus according to an embodiment.

As shown in FIG. 21, first, in Step 201, phase information 12 of a Moire fringe 30 is acquired. Then, in Step 202, a plurality of subject images 10 is acquired while relatively translating the subject 200 and the imaging system 40 by the moving mechanism 8. Then, in Step 203, the pixels of the subject 200 in the plurality of subject images 10 are associated with the phase values of the Moire fringe 30. Then, in Step 204, based on the intensity signal curve 32, the phase-contrast image 16 is generated. Note that in the case of generating a phase-contrast image 17 in which a plurality of phase-contrast images 16 is joined, it is sufficient to perform the processing of Steps 202 to 204 plural times.

Then, in Step 205, from the phase-contrast image 16 (17), the distribution 401 (501) of the pixel values of the phase-contrast image 16 (17) is acquired. Then, in Step 206, based on the distribution 401 (501) of the pixel values, a correction map 403 (503) is generated. Then, in Step 207, using the correction map 403 (503), the gradation 16d (17a) of the phase-contrast image 16 (17) is corrected and removed. Thereafter, the phase-contrast image generation processing is terminated.

Effects of this Embodiment

In this embodiment, the following effects can be obtained.

In this embodiment, as described above, the phase-contrast image 16 (17) is generated based on the plurality of subject images 10 acquired by the moving mechanism 8 while relatively translating the subject 200 and the imaging system 40, and the gradation 16d (17a) that occurred along the Y-direction (orthogonal direction) orthogonal to the X-direction (translation direction) as viewed from the optical axis direction of the X-ray in the phase-contrast image 16 (17) is corrected based on the distribution state of the gradation 16d (17a). Thus, since it is possible to remove the gradation 16d (17a) that occurred along the Y-direction orthogonal to the X-direction as viewed from the optical axis direction of the X-rays in the phase-contrast image 16 (17), the phase-contrast image 16(17) can be prevented from becoming difficult to see due to the gradation 16d (17a) that occurred in the phase-contrast image 16 (17).

Further, in this embodiment, as described above, the step of correcting the gradation 16d (17a) includes a step of correcting the gradation 16d (17a) based on the distribution 401 (501) of the pixel values of the phase-contrast image 16 (17) along the Y-direction (orthogonal direction). Thus, it is possible to correct the gradation 16d (17a) based on the distribution 401 (501) of the pixel values in which the distribution state of the gradation 16d (17a) is reflected, so that it is possible to easily remove the gradation 16d (17a) that occurred in the phase-contrast image 16 (17). Consequently, it is possible to easily suppress that the phase-contrast image 16 (17) becomes difficult to see due to the gradation 16d (17a) that occurred in the phase-contrast image 16 (17).

Further, in this embodiment, as described above, the step of correcting the gradation 16d (17a) includes a step of correcting the gradation 16d (17a) based on the distribution 401 (501) of the pixel values ranging from one end portion of the phase-contrast image 16 (17) to the other end portion thereof in the Y-direction (orthogonal direction). Thus, since it is possible to correct the gradation 16d (17a) based on the distribution 401 (501) of the pixel values of the entire range in the Y-direction, the gradation 16d (17a) that occurred in the phase-contrast image 16 (17) from one end portion in the Y-direction to the other end thereof can be removed over a wide range. Consequently, it is possible to widely suppress that the phase-contrast image 16 (17) becomes difficult to see due to the gradation 16d (17a) that occurred in the phase-contrast image 16 (17).

Further, in this embodiment, as described above, the step of correcting the gradation 16d (17a) includes a step of correcting the gradation 16d (17a) based on the distribution 401 (501) of the pixel values of the region of the phase-contrast image 16 (17) in which there exists no subject 200. Thus, as compared with the case of correcting the gradation 16d (17a) based on the distribution of the pixel values of the region in which there exists the subject 200, the gradation 16d (17a) can be corrected based on the distribution 401 (501) of the pixel values in which the distribution state of the gradation 16d (17a) is accurately reflected. Consequently, the gradation 16d (17a) that occurred in the phase-contrast image 16(17) can be removed accurately.

Further, in this embodiment, as described above, the step of correcting the gradation 16d (17a) includes a step of correcting the gradation 16d (17a) based on the distribution 401 (501) of the pixel values in the vicinity of the end of the phase-contrast image 16 (17) in the X-direction (translation direction). As a result, since the gradation 16d (17a) can be corrected based on the distribution 401 (501) of the pixel values in the vicinity of the end of the phase-contrast image 16 (17) in which the subject 200 is less likely to be reflected in the X-direction, it is possible to reliably correct the gradation 16d (17a) based on the distribution 401 (501) of the pixel values in the region in which there exists no subject 200.

Further, in this embodiment, as described above, the distribution 401 (501) of the pixel values is configured to be the distribution 401 (501) of the average pixel values of the pixel group having a predetermined width in the X-direction (translation direction). Thus, as compared with the case using the distribution of pixel values of a single pixel as the distribution 401 (501) of the pixel values, the distribution 401 (501) of the pixel values in which the distribution state of the gradation 16d (17a) is more accurately reflected can be used for the correction of the gradation 16d (17a).

Further, in this embodiment, as described above, the step of correcting the gradation 16d (17a) includes a step of correcting the gradation 16d (17a) based on the correction map 403 (503) generated by stretching the distribution 401 (501) of the pixel values in the X-direction (translation direction). Thus, it is possible to correct the gradation 16d (17a) based on the correction map 403 (503) generated by utilizing that the gradation 16d (17a) has a substantially uniform pixel value in the X-direction, so that the gradation 16d (17a) that occurred in the phase-contrast image 16 (17) can be reliably removed.

Further, in this embodiment, as described above, the step of correcting the gradation 16d (17a) includes a step of correcting the gradation 16d (17a) based on the correction map 403 (503) generated by stretching the pixel value distribution 401 (501) in the X-direction so as to have the same number of pixels as the number of pixels of the phase-contrast image 16(17) in the X-direction (translation direction). Thus, it is possible to correct the gradation 16d (17a) based on the correction map 403 (503) generated so as to correspond to the entire range of the phase-contrast image 16 (17) in the X-direction, so that the gradation 16d (17a) that occurred in the phase-contrast image 16 (17) can be removed extensively. Consequently, it is possible to widely suppress that the phase-contrast image 16 (17) becomes difficult to see due to the gradation 16d (17a) that occurred in the phase-contrast image 16 (17).

Further, in this embodiment, as described above, the step of correcting the gradation 16d (17a) includes a step of correcting the gradation 16d (17a) by dividing the phase-contrast image 16 (17) by the correction map 403 (503) or subtracting the correction map 403 (503) from the phase-contrast image 16 (17). This makes it possible to correct the gradation 16d (17a) simply by the division or the subtraction, so that the gradation 16d (17a) can be easily corrected.

In this embodiment, as described above, the step of correcting the gradation 16d (17a) includes a step of correcting the gradation 17a in the phase-contrast image 17 in which a plurality of phase-contrast images 16 is joined. Thus, even in the phase-contrast image 17 in which a plurality of phase-contrast images 16 is joined, it is possible to suppress that the phase-contrast image 17 becomes difficult to see due to the gradation 17a.

In this embodiment, as described above, the phase-contrast image 16 (17) is configured to include the phase differential image 16b and the dark-field image 16c. Thus, in the phase differential image 16b and the dark-field image 16c in which the gradation 16d (17a) is likely to occur, it is possible to correct the gradation 16d (17a).

Modified Embodiments

It should be understood that the embodiments disclosed here are examples in all respects and are not restrictive. The scope of the present invention is shown in the claims rather than by the aforementioned embodiments, and the scope of the present invention includes all modifications (modified examples) within the meanings and ranges equivalent to the claims.

For example, the above-described embodiment shows an example in which the X-ray phase imaging apparatus 100 has three gratings 2 to 4, but the present invention is not limited thereto. In the present invention, the X-ray imaging device does not necessarily have to include three gratings. For example, in cases where the coherence of the X-rays emitted from the X-ray source is sufficiently high, it is not necessary to provide the grating 4 of the above-described embodiment. When the self-image of the grating can be directly detected by the detector, the grating 3 of the above-described embodiment does not have to be provided.

In the above-described embodiment, an example is shown in which the grating moving mechanism 9 moves the grating 2, but the present invention is not limited thereto. In the present invention, the grating to be moved may be any grating.

In the above-described embodiment, an example is shown in which the moving mechanism 8 is configured to translate the subject 200, but the present invention is not limited thereto. In the present invention, the moving mechanism may be configured to translate the imaging system.

In the above-described embodiment, an example is shown in which the subject 200 is moved to and stopped at the respective imaging positions (first to sixth imaging positions) and the subject 200 is repeatedly imaged to acquire a plurality of subject images 10, but the present invention is not limited thereto. In the present invention, a plurality of subject images may be acquired by imaging while continuously moving the subject without stopping it. That is, after capturing the image of the subject as a moving image, a plurality of subject images may be acquired from the moving image of the subject.

Figure 22:
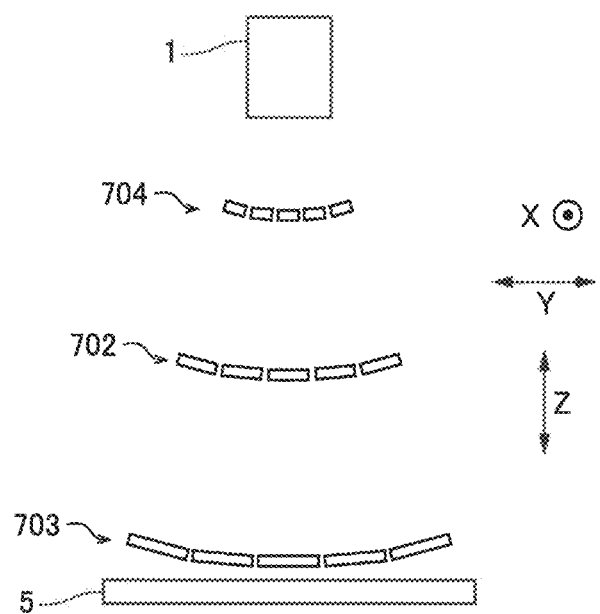
FIG. 22 is a schematic diagram for explaining the configuration of an X-ray phase imaging apparatus according to a modification of an embodiment.

In the above-described embodiment, an example is shown in which the gratings 2 to 4 are each formed in a flat plate shape, but the present invention is not limited thereto. In the present invention, the grating may be formed in a shape other than a flat shape. For example, in the variation shown in FIG. 22, gratings 702, 703, and 704 are formed to be curved. Specifically, the gratings 702, 703, and 704 are each formed to have a curved convex shape with protruding toward detector 5 side from the X-ray source 1 side. Thus, it is possible to increase the field of view of the X-ray phase imaging apparatus.

In the above-described embodiment, an example is shown in which the X-ray phase imaging apparatus 100 is configured to move the subject 200 between the grating 2 and the grating 3, but the present invention is not limited thereto. In the present invention, the X-ray phase imaging apparatus may be configured to move the subject between the X-ray source 1 and the grating 2 of the embodiment.

In the above-described embodiment, an example is shown in which the image processing unit 6 is configured to correct the gradation 16d (17a) based on the distribution 401 (501) of the pixel values from one end of the phase-contrast image 16 (17) in the Y-direction to the other end thereof, but the present invention is not limited thereto. In the present invention, as long as it is possible to correct the gradation of the subject reflected in at least the phase-contrast image, the image processing unit may be configured to correct the gradation based on the distribution of the pixel values of a part of the phase-contrast image in the Y-direction.

In the above-described embodiment, an example is shown in which the image processing unit 6 is configured to correct the gradation 16d (17a) based on the distribution of the pixel values in the vicinity of the end of the phase-contrast image 16 (17) in the X-direction, but the present invention is not limited thereto. In the present invention, as long as the distribution is the pixel values of the region in which there exists no subject, the image processing unit may be configured to correct the gradation based on the distribution of the pixel values of the portion other than the vicinity of the end of the phase-contrast image in the X-direction.

In the above-described embodiment, an example is shown in which the distribution 401 (501) of the pixel values is a distribution of the average pixel values of the pixel group having the predetermined widths 402 (502) in the X-direction, but the present invention is not limited thereto. In the present invention, the distribution of the pixel values may be a distribution of the pixel values of a single pixel, provided that the distribution state of the gradation is reflected.

In the above-described embodiment, an example is shown in which the image processing unit 6 is configured to generate the correction map 403 (503) by stretching the distribution 401 (501) of the pixel values in the X-direction so that the number of pixels has the same number of pixels as the number of pixels of the phase-contrast image 16 (17) in the X-direction, but the present invention is not limited thereto. The present invention may be configured to generate a correction map by stretching the phase-contrast image of the pixel values in the X-direction such that the pixel number becomes less than the number of pixels of the phase-contrast image in the X-direction, as long as at least the gradation of the subject reflected in the phase-contrast image can be corrected. Further, the image processing unit may be configured to generate a correction map by stretching the distribution of the pixel values in the X-direction so that the number of pixels is greater than the number of pixels of the phase-contrast image in the X-direction.

(Aspects)

It will be understood by those skilled in the art that the above-described exemplary embodiments are concrete examples of the following aspects.

(Item 1)

An X-ray phase imaging method comprising:

a step of acquiring a plurality of images while relatively translating a subject and an imaging system composed of an X-ray source, a detector configured to detect X-rays emitted from the X-ray source, and a plurality of gratings arranged between the X-ray source and the detector;

a step of generating a phase-contract image based on the plurality of images; and a step of correcting a gradation that occurred along an orthogonal direction to a translation direction as viewed from an optical axis direction of the X-rays in the phase-contrast image based on a distribution state of the gradation.

(Item 2)
The X-ray phase imaging method as recited in Item 1, wherein the step of correcting the gradation includes a step of correcting the gradation based on a distribution of pixel values of the phase-contrast image along the orthogonal direction.

(Item 3)
The X-ray phase imaging method as recited in Item 2, wherein the step of correcting the gradation includes a step of correcting the gradation based on a distribution of pixel values of the phase-contrast image ranging from one end of the phase-contrast image in the orthogonal direction to the other end thereof.

(Item 4)
The X-ray phase imaging method as recited in Item 2 or 3, wherein the step of correcting the gradation includes a step of correcting the gradation based on the distribution of the pixel values of a region of the phase-contrast image in which there exists no subject.

(Item 5)
The X-ray phase imaging method as recited in Item 4, wherein the step of correcting the gradation includes a step of correcting the gradation based on the distribution of the pixel values in the vicinity of an end of the phase-contrast image in the translation direction.

(Item 6)
The X-ray phase imaging method as recited in any one of Items 2 to 5, wherein the distribution of the pixel values is a distribution of average pixel values of a pixel group having a predetermined width in the translation direction.

(Item 7)
The X-ray phase imaging method as recited in any one of Items 2 to 6, wherein the step of correcting the gradation includes a step of correcting the gradation based on a correction map generated by stretching the distribution of the pixel values in the translation direction.

(Item 8)
The X-ray phase imaging method as recited in Item 7, wherein the step of correcting the gradation includes a step of correcting the gradation based on the correction map generated by stretching the distribution of the pixel values in the translation direction so that the number of pixels becomes the same as the number of pixels of the phase-contrast image in the translation direction.

(Item 9)
The X-ray phase imaging method as recited in Item 7 or 8, wherein the step of correcting the gradation includes a step of correcting the gradation by dividing the phase-contrast image by the correction map or subtracting the correction map from the phase-contrast image.

(Item 10)
The X-ray phase imaging method as recited in any one of Items 1 to 9, wherein the step of correcting the gradation includes a step of correcting the gradation in the phase-contrast image in which a plurality of phase-contrast images is joined together.

(Item 11)
The X-ray phase imaging method as recited in any one of Items 1 to 10, wherein the phase-contrast image includes a phase differential image and a dark-field image.

The invention claimed is:

1. An X-ray phase imaging method comprising:
a step of acquiring a plurality of images while relatively translating a subject and an imaging system composed of an X-ray source, a detector configured to detect X-rays emitted from the X-ray source, and a plurality of gratings arranged between the X-ray source and the detector;
a step of generating a phase-contract image based on the plurality of images; and
a step of correcting a gradation that occurred along an orthogonal direction to a translation direction as viewed from an optical axis direction of the X-rays in the phase-contrast image based on a distribution state of the gradation.

2. The X-ray phase imaging method as recited in claim 1, wherein the step of correcting the gradation includes a step of correcting the gradation based on a distribution of pixel values of the phase-contrast image along an orthogonal direction.

3. The X-ray phase imaging method as recited in claim 2, wherein the step of correcting the gradation includes a step of correcting the gradation based on a distribution of pixel values of the phase-contrast image ranging from one end of the phase-contrast image in the orthogonal direction to the other end thereof.

4. The X-ray phase imaging method as recited in claim 2, the step of correcting the gradation includes a step of correcting the gradation based on the distribution of the pixel values of a region of the phase-contrast image in which there exists no subject.

5. The X-ray phase imaging method as recited in claim 4, wherein the step of correcting the gradation includes a step of correcting the gradation based on the distribution of the pixel values in the vicinity of an end of the phase-contrast image in the translation direction.

6. The X-ray phase imaging method as recited in claim 2, wherein the distribution of the pixel values is a distribution of average pixel values of a pixel group having a predetermined width in the translation direction.

7. The X-ray phase imaging method as recited in claim 2, wherein the step of correcting the gradation includes a step of correcting the gradation based on a correction map generated by stretching the distribution of the pixel values in the translation direction.

8. The X-ray phase imaging method as recited in claim 7, wherein the step of correcting the gradation includes a step of correcting the gradation based on the correction map generated by stretching the distribution of the pixel values in the translation direction so that the number of pixels becomes the same as the number of pixels of the phase-contrast image in the translation direction.

9. The X-ray phase imaging apparatus method as recited in claim 7, wherein the image processing unit the step of correcting the gradation includes a step ofis configured to correcting the gradation by dividing the phase-contrast image by the correction map or subtracting the correction map from the phase-contrast image.

10. The X-ray phase imaging apparatus method as recited in claim 1, wherein the image processing unit the step of correcting the gradation includes a step ofis configured to correcting the gradation in the phase-contrast image in which a plurality of phase-contrast images is joined together.

11. The X-ray phase imaging apparatus method as recited in claim 1, wherein the phase-contrast image includes a phase differential image and a dark- field image.

* * * * *